(12) United States Patent
Jang et al.

(10) Patent No.: US 10,251,557 B2
(45) Date of Patent: Apr. 9, 2019

(54) MODULATOR ARRAYS, AND MODULATION DEVICES AND MEDICAL IMAGING APPARATUSES INCLUDING THE SAME

(71) Applicant: SAMSUNG ELECTRONICS CO., LTD., Suwon-si (KR)

(72) Inventors: Jae-duck Jang, Suwon-si (KR); Jae-guyn Lim, Seongnam-si (KR); Woo-young Jang, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1038 days.

(21) Appl. No.: 14/313,349

(22) Filed: Jun. 24, 2014

(65) Prior Publication Data
US 2015/0094572 A1   Apr. 2, 2015

(30) Foreign Application Priority Data
Sep. 30, 2013   (KR) .................. 10-2013-0116895

(51) Int. Cl.
*A61B 5/00* (2006.01)
*G02F 1/13* (2006.01)
*G02F 1/1347* (2006.01)

(52) U.S. Cl.
CPC .......... *A61B 5/0084* (2013.01); *A61B 5/0066* (2013.01); *A61B 5/0095* (2013.01); *G02F 1/1313* (2013.01); *G02F 1/13471* (2013.01); *G02F 2203/50* (2013.01)

(58) Field of Classification Search
CPC .. G02B 6/3885; G02B 6/3887; G02B 5/1828; G02B 3/0025; G02B 3/0031; G02B 7/022; A61B 3/102; A61B 3/14
See application file for complete search history.

(56) References Cited

U.S. PATENT DOCUMENTS

| | | | |
|---|---|---|---|
| 4,399,356 A | 8/1983 | Feinleib et al. | |
| 7,431,461 B2 | 10/2008 | Nitta et al. | |
| 7,670,005 B2 | 3/2010 | Pate et al. | |
| 7,791,734 B2 | 9/2010 | Olivier et al. | |
| 8,842,222 B2 | 9/2014 | Iversen | |
| 8,958,032 B2 | 2/2015 | Gu | |
| 9,870,759 B2 | 1/2018 | Oh et al. | |
| 2006/0051022 A1 | 3/2006 | Levner et al. | |
| 2007/0258095 A1* | 11/2007 | Olivier | A61B 3/102 356/479 |
| 2010/0165134 A1* | 7/2010 | Dowski, Jr. | B24B 13/06 348/218.1 |
| 2010/0214282 A1 | 8/2010 | Whitehead et al. | |
| 2013/0057826 A1 | 3/2013 | Hanebuchi | |

FOREIGN PATENT DOCUMENTS

| | | |
|---|---|---|
| JP | 2013-052047 A | 3/2013 |
| WO | 2008/020899 A2 | 2/2008 |

* cited by examiner

*Primary Examiner* — Joel Lamprecht
(74) *Attorney, Agent, or Firm* — Sughrue Mion, PLLC

(57) ABSTRACT

The modulator array includes a first optical modulator, which changes a shape a wavefront of an incident light into first wavefronts to modulate the incident light which passes through the first optical modulator; and a second optical modulator that changes a shape at least one of the first wavefronts into second wavefronts to modulate the light output from the first optical modulator.

20 Claims, 9 Drawing Sheets

MODULATOR ARRAYS, AND MODULATION DEVICES AND MEDICAL IMAGING APPARATUSES INCLUDING THE SAME

CROSS-REFERENCE TO RELATED APPLICATION

This application claims priority from Korean Patent Application No. 10-2013-0116895, filed on Sep. 30, 2013, in the Korean Intellectual Property Office, the disclosure of which is incorporated herein in its entirety by reference.

BACKGROUND

1. Field

The present disclosure relates to modulator arrays, and modulation devices and medical imaging apparatuses including the same.

2. Description of the Related Art

In the medical imaging field, the demand for information about a tissue of a living body and for imaging technologies are increasing.

For example, many cancers occur under an epithelial cell, and metastasize inside a hypodermal cell. Therefore, when it is possible to early detect cancer, a damage caused by the cancer is considerably reduced. A related art imaging technology uses a magnetic resonance imaging (MRI), a computed tomography (CT), ultrasound, or the like, to image an internal tomography through the skin. However, since the image resolution is low, it is impossible to early detect a small-size cancer.

On the other hand, an optical coherence tomography (OCT), an optical coherence microscopy (OCM), and a photoacoustic tomography (PAT) may use light to diagnose early stages of cancer. Although a skin penetration depth may be as low as 1 mm to 2 mm, for the OCT, or 50 mm to 50 mm, for the PAT, a resolution is higher by about ten to twenty times than, for example, of the ultrasound, and, thus, these technologies may usefully diagnose incipient cancer.

Thus, in these technologies, there is a need for apparatuses and methods to achieve the light with a controllable wavefront, to be capable of capturing an image deep inside of a bio-tissue, even when the skin tissue penetration of the incident light is low.

SUMMARY

Exemplary embodiments address at least the above problems and/or disadvantages and other disadvantages not described above. Also, the exemplary embodiments are not required to overcome the disadvantages described above, and may not overcome any of the problems described above.

One or more exemplary embodiments provide modulator arrays that control a wavefront of light by using a plurality of optical modulators, and modulation devices and medical imaging apparatuses including the same.

According to an exemplary embodiment, a modulator array includes: a first optical modulator that shapes a wavefront of light into a plurality of first shape wavefronts to modulate the light; and a second optical modulator that shapes at least one of the plurality of first wavefronts into a plurality of second shape wavefronts to modulate the light output from the first optical modulator.

A boundary between adjacent wavefronts of the plurality of second shape wavefronts may be discontinuous.

The first and second optical modulators may partially overlap each other with respect to a path of propagation of light.

The first and second optical modulators may be arranged cornerwise with respect to a vertical direction of the path of propagation of light.

At least one of the first and second optical modulators may include a plurality of cells that modulate at least one of a size and a phase of incident light.

The plurality of cells may be arranged vertically to the path of propagation of light.

Adjacent cells of the plurality of cells modulate incident light into light having different phases.

At least one cell included in the first optical modulator may overlap a plurality of cells included in the second optical modulator.

At least one of the first and second optical modulators may include at least one of liquid crystal on silicon (LCoS) and a deformable mirror (DM).

A first driving signal of the first optical modulator and a second driving signal of the second optical modulator may be synchronized with each other.

The first and second driving signals may have the same period and different phases.

A phase difference between the first and second driving signals may be shorter than a period of the first driving signal.

According to an exemplary embodiment, a modulation device includes: the modulator array; and a modulation controller that controls at least one of a position and a driving signal of at least one optical modulator of the modulator array to increase a modulation resolution of light passing through the modulator array.

The modulation controller may control a degree of overlapping between the optical modulators of the modulator array with respect to a path of propagation of light.

The modulation controller may control at least one of the first and second optical modulators so that one cell of the first optical modulator overlaps a plurality of cells included in the second optical modulator.

The modulation controller may move at least one of the first and second optical modulators in a vertical direction of the path of propagation of light.

The modulation controller may control a phase difference between a first driving signal of the first optical modulator and a second driving signal of the second optical modulator.

The phase difference may be shorter than a period of the first driving signal.

According to an exemplary embodiment, a medical imaging apparatus includes: a light source; the modulator array that modulates light output from the light source; and a probe that is inserted into a body cavity, and irradiates light, output from the modulator array, onto an internal object of the body cavity.

The medical imaging apparatus may further include an interferometer that splits the light, output from the modulator array, into measurement light and reference light, transfers the measurement light to the probe, and receives response light corresponding to the measurement light from the probe to cause coherence between the measurement light and the reference light, wherein the medical imaging apparatus may use an optical coherence tomography (OCT) technology.

BRIEF DESCRIPTION OF THE DRAWINGS

The above and/or other aspects will be more apparent by describing certain exemplary embodiments with reference to the accompanying drawings, in which.

DETAILED DESCRIPTION

Figure 1:
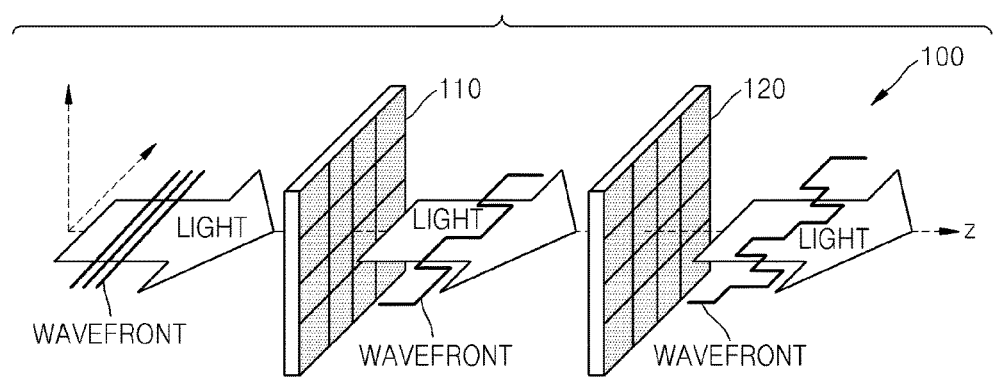
FIG. 1 is a diagram illustrating a modulator array according to an exemplary embodiment.

Exemplary embodiments are described in greater detail with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

Expressions such as "at least one of," when preceding a list of elements, modify the entire list of elements and do not modify the individual elements of the list. In the drawings, the size of each element may be exaggerated for clarity and convenience of description.

FIG. 1 is a diagram illustrating a modulator array 100 according to an exemplary embodiment. As illustrated in FIG. 1, the modulator array 100 may include a first optical modulator 110, which shapes a wavefront of incident light into a plurality of first shape wavefronts to modulate the light, and a second optical modulator 120 that shapes at least one of the plurality of first wavefronts into a plurality of second shape wavefronts to modulate the light output from the first optical modulator 110. The shape wavefront is a partial region of a wavefront. Internal dots of the shape wavefront are continuous, but a boundary between the shape wavefronts is discontinuous. This is because below-described cells modulate light to have different phases.

The first and second optical modulators 110 and 120 are disposed on a path of propagation of light. Therefore, the light is primarily modulated by the first optical modulator 110 as the incident light passes, and is secondarily modulated by the second optical modulator 120 as the primarily-modulated light passes. Each of the first and second optical modulators 110 and 120 may be configured with a plurality of cells that modulate at least one of a size and a phase of incident light. Adjacent cells of the plurality of cells modulate incident light to have different phases. The plurality of cells may be arranged in a direction across a path of propagation of light, and may be arranged primarily or secondarily.

The first optical modulator 110 may spatially shape light. The first optical modulator 110 may be at least one of liquid crystal on silicon (LCoS) and a deformable mirror (DM).

The LCoS is manufactured by coating liquid crystal on a surface of a silicon wafer, and thus reflects incident light to modulate the incident light. Phase modulation of light may be changed according to a position of the liquid crystal, and the position of the liquid crystal may be changed according to a driving signal, for example, an applied voltage. One LCoS may shape a wavefront of the incident light into a plurality of shape wavefronts. Here, each of some regions of the LCoS, which modulates the incident light to have the same phase, may be a cell. In the first optical modulator 110, a plurality of the LCoS may be arranged, and one LCoS may modulate the incident light to have the same phase. In this case, each of the plurality of the LCoS may be a cell.

The DM deforms a shape of a reflective surface to modulate light. Phase modulation of the light may be changed according to a bent shape of the reflective surface, and the shape of the reflective surface may be changed according to a driving signal, for example, an applied voltage. One DM may shape a wavefront of incident light into a plurality of shape wavefronts. Here, each of some regions of the DM, which modulates the incident light to have the same phase, may be a cell. In the first optical modulator 110, a plurality of the DMs may be arranged, and one DM may modulate the incident light to have the same phase. In this case, each of the plurality of DMs may be a cell.

The second optical modulator 120 is disposed on the path of propagation of light, and light obtained through modulation by the first optical modulator 110 is incident onto the second optical modulator 120. The second optical modulator 120 may additionally shape a shape wavefront of the incident light with respect to at least one of a space and a time. The second optical modulator 120 may be at least one of the LCoS and the DM.

The first and second optical modulators 110 and 120 may be disposed to overlap some regions thereof with respect to the path of propagation of light. Therefore, at least one of a plurality of shape wavefronts obtained through shaping by the first optical modulator 110 may be shaped into a plurality of shape wavefronts while passing through the second optical modulator 120. In FIG. 1, for convenience of description, the modulator array 100 is illustrated as including the first and second optical modulators 110 and 120, but the modulator array 100 may include three or more optical modulators.

Figure 2:
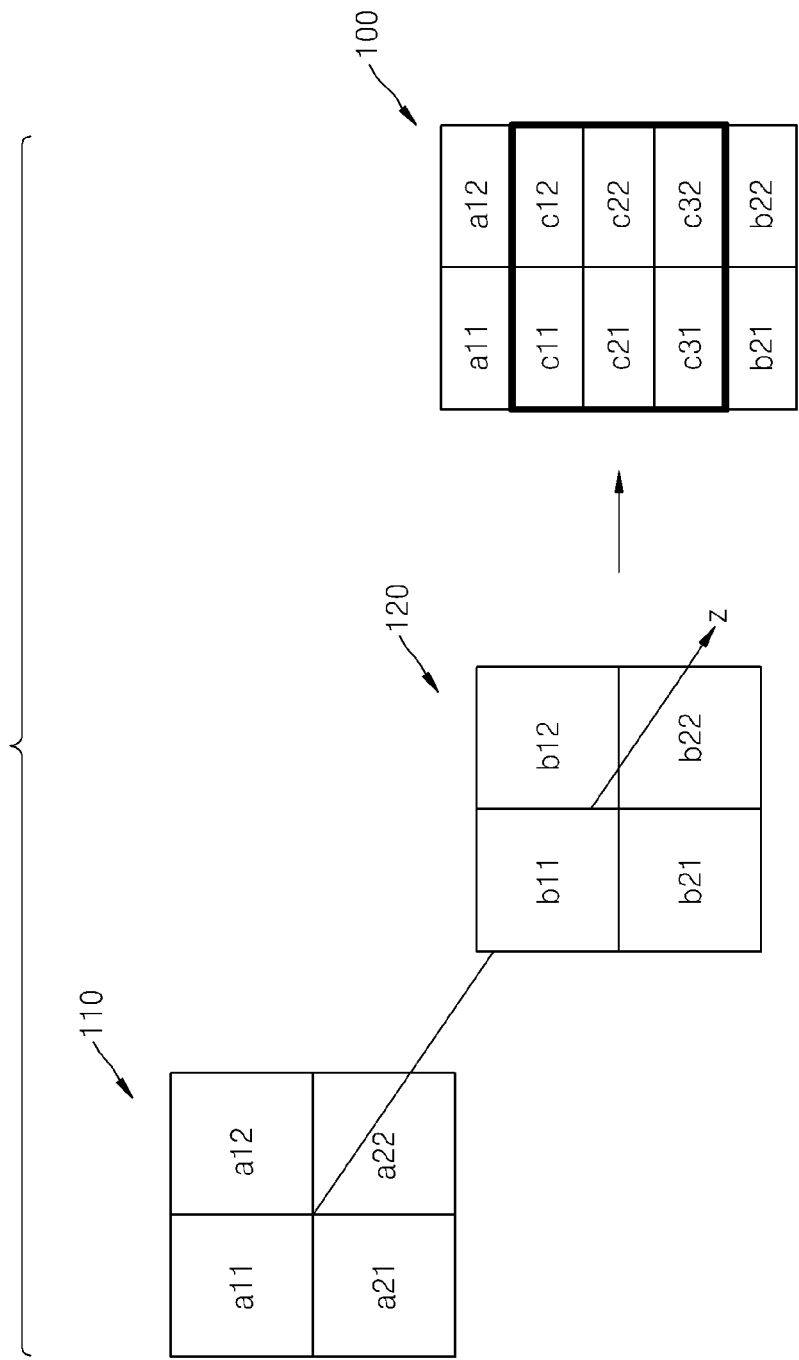
FIGS. 2, 3, and 4 are diagrams exemplarily illustrating an arrangement relationship between first and second optical modulators.
Figure 3:
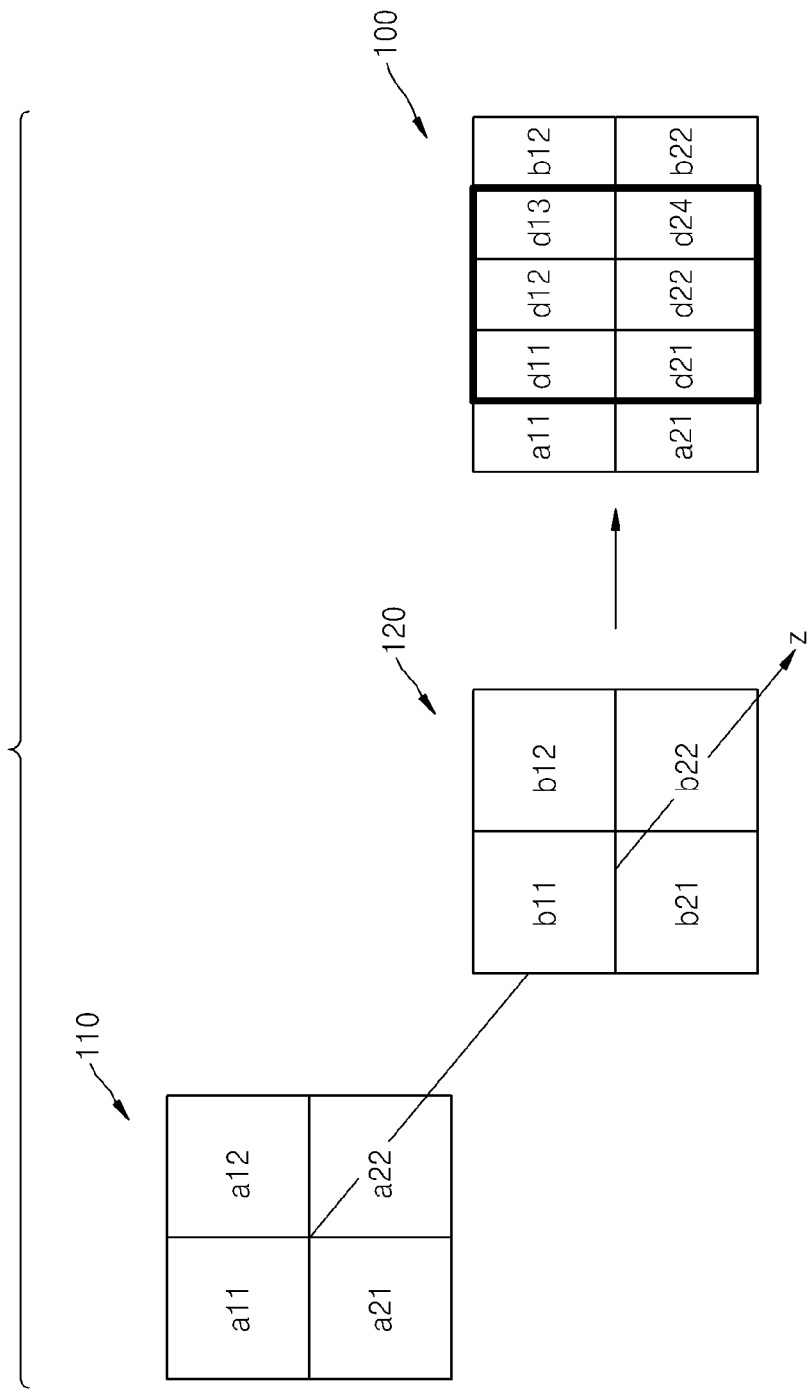
Figure 4:
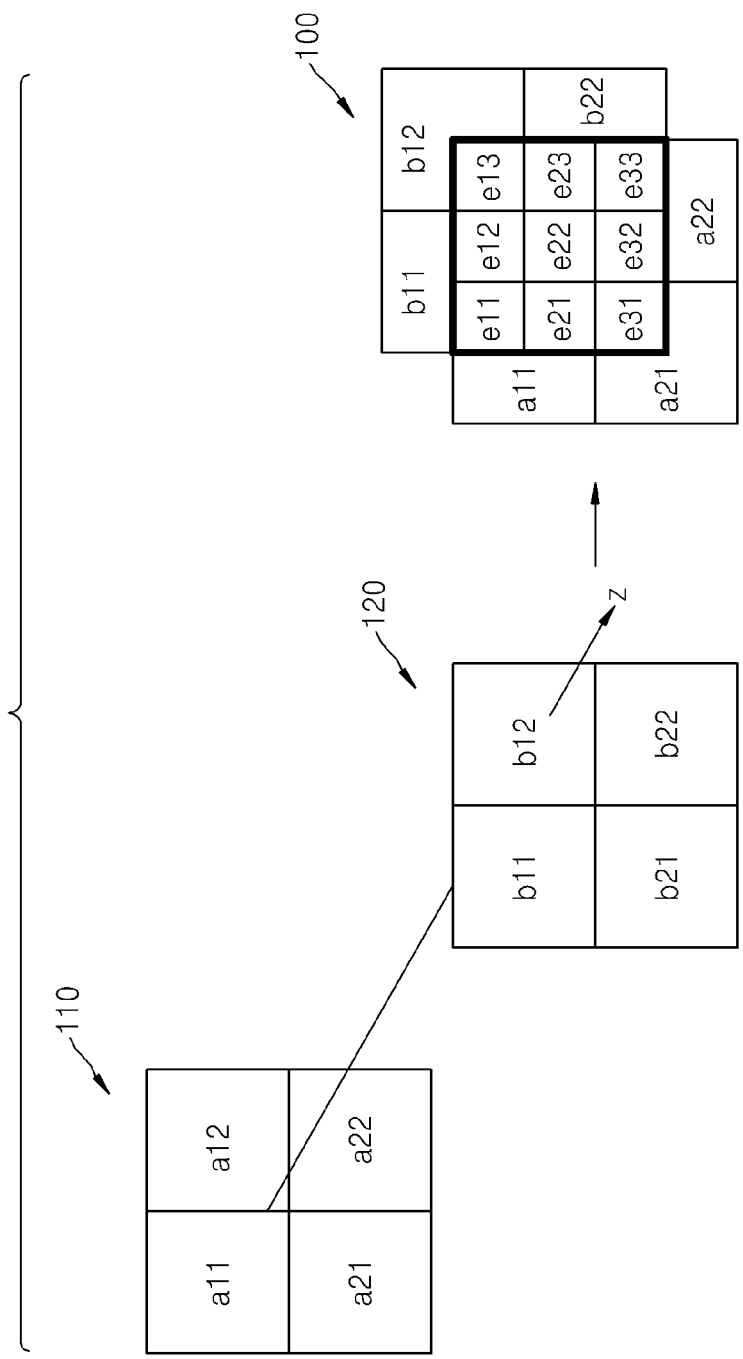

FIGS. 2 to 4 are diagrams exemplarily illustrating an arrangement relationship between first and second optical modulators 110 and 120. For convenience of description, it is assumed that the number of cells of the first optical modulator 110 is the same as the number of cells of the second optical modulator 120. However, the assumption is only for convenience of description, and the present exemplary embodiment is not limited thereto. The number of cells of the first optical modulator 110 may differ from the number of cells of the second optical modulator 120.

As illustrated in FIG. 2, the first optical modulator 110 may include four cells a11, a12, a21 and a22. Adjacent cells modulate a wavefront of incident light into a plurality of shape wavefronts having different phases. Therefore, a wavefront of light incident onto the first optical modulator 110 may be modulated into four different shape wavefronts, and the modulated light may be output.

The second optical modulator 120 may be disposed in a lower direction with respect to the first optical modulator 110, i.e., in a direction parallel to the Y-axis (illustrated in FIG. 1) and perpendicular to a direction of the incident light in FIG. 2. First and second cells a11 and a12 of the first optical modulator 110 may partially overlap first and second cells b11 and b12 of the second optical modulator 120, and third and fourth cells a21 and a22 of the first optical modulator 110 may partially overlap first and third cells b11 and b21 and second and fourth cells b12 and b22 of the second optical modulator 120, respectively. A wavefront of light incident onto the modulator array 100 is output as the following shape wavefront according to the position arrangement of the first and second optical modulators 110 and 120.

Specifically, a portion of a shape wavefront of light obtained through modulation by the first cell a11 of the first optical modulator 110 is modulated by the first cell b11 of the second optical modulator 120. Therefore, light incident onto the first cell a11 of the first optical modulator 110 of the modulator array 100 may be output as two shape wavefronts having different phases. That is, in the modulator array 100, the light incident onto the first cell a11 of the first optical modulator 110 may be modulated into two shape wavefronts having different phases by the first cell a11 and a first overlapping cell c11, and the modulated shape wavefronts may be output. Here, an overlapping cell is a region in which the cell of the first optical modulator 110 overlaps the cell of the second optical modulator 120, and light is modulated by the first and second optical modulators 110 and 120.

A portion of a shape wavefront of light obtained through modulation by the second cell a12 of the first optical modulator 110 is modulated by the second cell b12 of the second optical modulator 120. Therefore, in the modulator array 100, light incident onto the second cell a12 of the first optical modulator 110 may be modulated into two shape wavefronts having different phases by the second cell a12 and the first overlapping cell c12, and the modulated shape wavefronts may be output.

Similarly, a shape wavefront of light obtained through modulation by the third cell a21 of the first optical modulator 110 is modulated by the first and third cells b11 and b21 of the second optical modulator 120, and is output as two shape wavefronts having different phases, and thus, light incident onto the third cell a21 of the first optical modulator 110 is modulated into two shape wavefronts having different phases by third and fifth overlapping cells c21 and c31. A shape wavefront of light obtained through modulation by the fourth cell b22 of the second optical modulator 120 is also modulated into two shape wavefronts having different phases by the second and fourth cells b12 and b22 of the second optical modulator 120, and the modulated shape wavefronts are output. That is, light incident onto the fourth cell a22 of the first optical modulator 110 is the same as a result in which the light is modulated into two shape wavefronts having different phases by fourth and sixth overlapping cells c22 and c32. In addition, although not passing through the first optical modulator 110, there may be light that passes through the third and fourth cells b21 and b22 of the second optical modulator 120. The light passing through the third and fourth cells b21 and b22 of the second optical modulator 120 is phase-modulated and output. Therefore, light passing through the first and second optical modulators 110 and 120 is output as light having six shape wavefronts in an overlapping region between the first and second optical modulators 110 and 120. As a result, each of the optical modulators includes four cells, but when the optical modulators are arranged to overlap each other, light may be modulated by eight cells.

The first and second optical modulators 110 and 120 may be arranged with a displacement in a left or right direction with respect to the path of propagation of light, i.e., in a direction parallel to the X-axis (illustrated in FIG. 1) and perpendicular to a direction of the incident light in FIG. 2, and may partially overlap each other.

For example, as illustrated in FIG. 3, a wavefront of light incident onto the first optical modulator 110 is modulated into four different shape wavefronts, and the modulated shape wavefronts are output. The second optical modulator 120 is disposed conerwise in a right direction with respect to the first optical modulator 110. The first and third cells a11 and a21 of the first optical modulator 110 overlap the first and third cells b11 and b21 of the second optical modulator 120, and the second and fourth cells a12 and a22 of the first optical modulator 110 may partially overlap the first and second cells b11 and b12 and the third and fourth cells b21 and b22 of the second optical modulator 120, respectively. A wavefront of light incident onto the modulator array 100 may be modulated as follows according to the position arrangement of the first and second optical modulators 110 and 120.

Specifically, a portion of a shape wavefront of light obtained through modulation by the first cell a11 of the first optical modulator 110 is modulated by the first cell b11 of the second optical modulator 120, and a portion of a shape wavefront of light obtained through modulation by the third cell a21 of the first optical modulator 110 is modulated by the third cell b21 of the second optical modulator 120. That is, in the modulator array 100, light incident onto the first cell a11 of the first optical modulator 110 is modulated into two shape wavefronts having different phases by the first cell a11 and the first overlapping cell c11, and light incident onto the third cell a21 of the first optical modulator 110 is modulated by the third cell a21 and a fourth overlapping cell d31.

A shape wavefront of light obtained through modulation by the second cell a12 of the first optical modulator 110 is modulated by the first cell b11 and second cell b12 of the second optical modulator 120, and is thereby output as two shape wavefronts having different phases. A shape wavefront of light obtained through modulation by the fourth cell b22 of the second optical modulator 120 is modulated by the third and fourth cells b21 and b22 of the second optical modulator 120, and is thereby output as two shape wavefronts having different phases. That is, in the modulator array 100, light incident onto the second cell a12 of the first optical modulator 110 is modulated by second and third overlapping cells d12 and d13, and light incident onto the fourth cell a23 of the first optical modulator 110 is modulated by the fourth and fifth overlapping cells d22 and d23.

Therefore, light passing through the first and second optical modulators 110 and 120 is output as light having six shape wavefronts in the overlapping region between the first and second optical modulators 110 and 120.

The first and second optical modulators 110 and 120 may be arranged cornerwise in a diagonal direction with respect to the path of propagation of light, and may partially overlap each other. For example, as illustrated in FIG. 4, the second optical modulator 120 is disposed conerwise in a right upper direction with respect to the first optical modulator 110. The modulator array 100 may form a first overlapping cell e11 by overlapping between the first cell a11 of the first optical modulator 110 and the first cell b11 of the second optical modulator 120, and may form a fourth overlapping cell e21 by overlapping between the first cell a11 of the first optical modulator 110 and the third cell b21 of the second optical modulator 120. Also, the modulator array 100 may form second, third, fifth, and sixth overlapping cells e12, e13, e22 and e23 by overlapping between the second cell a12 of the first optical modulator 110 and the first to fourth cells b11, b12, b21 and b22 of the second optical modulator 120. The modulator array 100 may form a seventh overlapping cell e31 by overlapping between the third cell a21 of the first optical modulator 110 and the third cell b21 of the second optical modulator 120, and may form eighth and ninth overlapping cells e32 and e33 by overlapping between the fourth cell a22 of the first optical modulator 110 and the third and fourth cells b21 and b22 of the second optical modulator 120.

Therefore, light passing through the modulator array 100 is output as light having nine shape wavefronts in the overlapping region between the first and second optical modulators 110 and 120.

Figure 5:
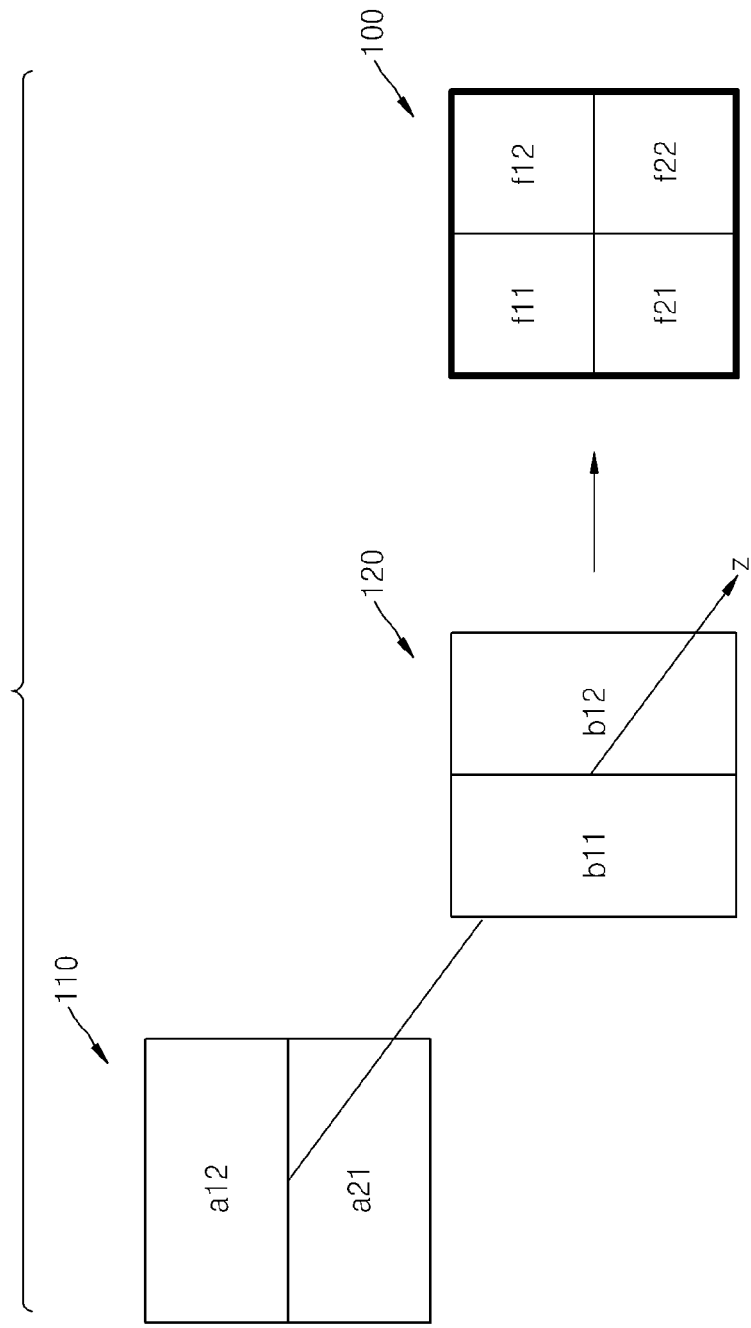
FIGS. 5 and 6 are exemplary diagrams for describing an overlapping relationship between a plurality of optical modulators according to an exemplary embodiment.
Figure 6:
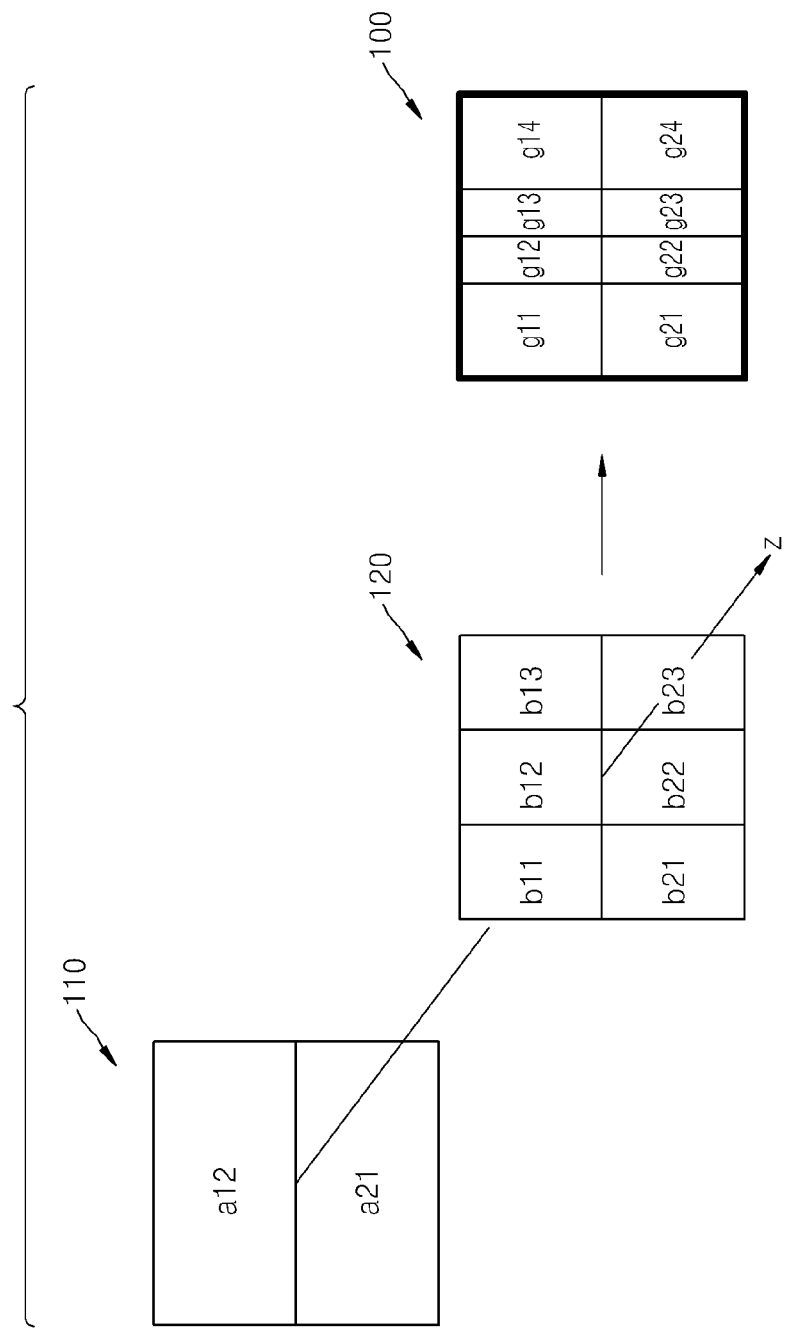

FIGS. 5 and 6 are exemplary diagrams for describing an overlapping relationship between a plurality of optical modulators according to an exemplary embodiment.

As illustrated in FIG. 5, the cell arrangement a11 and a21 of the first optical modulator 110 may differ from the cell arrangement b11 and b12 of the second optical modulator 120. Therefore, the modulator array 100 forms four overlapping cells f11, f12, f21 and f22 by overlapping between the first and second optical modulators 110 and 120. As a result, the first optical modulator 110 may shape a wavefront of light into a plurality of shape wavefronts, and the second optical modulator 120 may shape at least one of a plurality of shape wavefronts, obtained through shaping by the first optical modulator 110, into a plurality of shape wavefronts.

As illustrated in FIG. 6, the number of cells a11 and a21 of the first optical modulator 110 may differ from the number of cells b11 and b12 of the second optical modulator 120. Therefore, the modulator array 100 forms eight overlapping cells g11 to g24 by overlapping between the first and second optical modulators 110 and 120. As a result, the first optical modulator 110 may shape a wavefront of light into a plurality of shape wavefronts, and the second optical modulator 120 may shape at least one of a plurality of shape wavefronts, obtained through shaping by the first optical modulator 110, into a plurality of shape wavefronts.

As described above, in arranging a plurality of optical modulators with respect to the path of propagation of light, when one cell of the first optical modulator 110 is disposed to overlap a plurality of cells of the second optical modulator 120, light passing through the modulator array 100 may be modulated into light having more shape wavefronts. Therefore, the modulator array 100 increases a space resolution of modulation. When the space resolution of modulation increases, light obtained through modulation by different optical modulators increases an energy efficiency in the path of propagation of light, thereby increasing a transmission depth.

Figure 7:
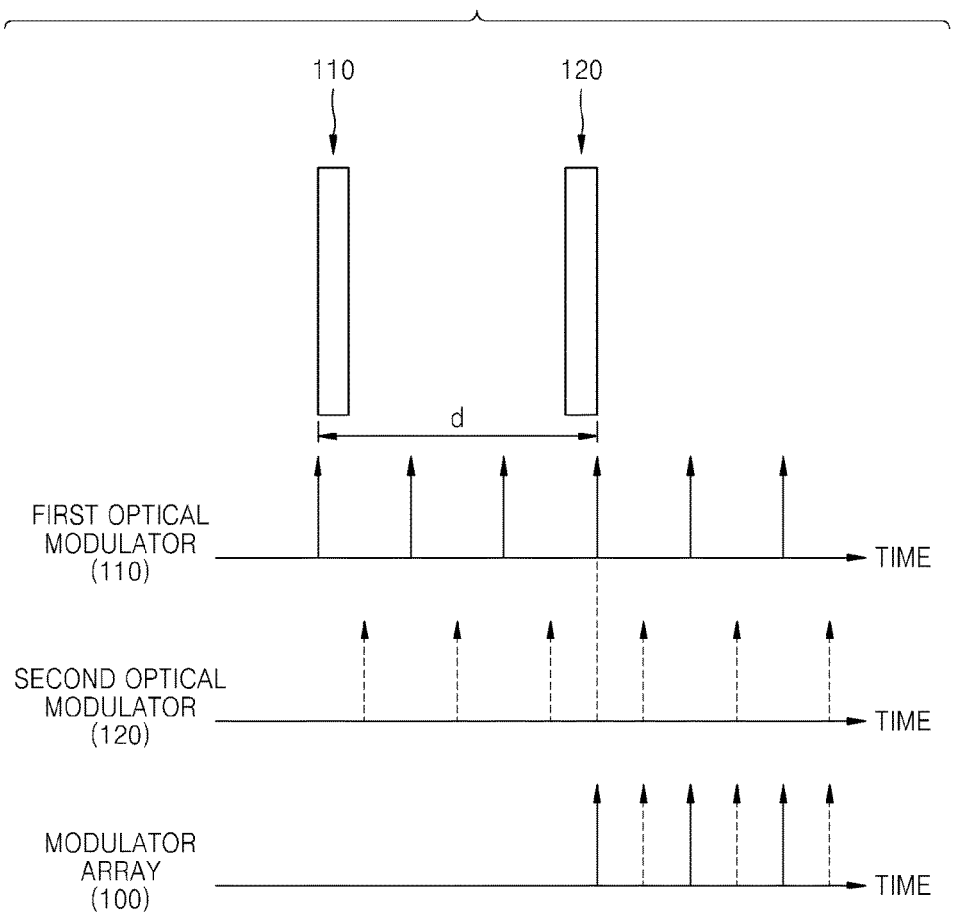
FIG. 7 is a reference diagram for describing a method of increasing a time resolution according to an exemplary embodiment.

Moreover, the modulator array 100 increases a time resolution of modulation. FIG. 7 is a reference diagram for describing a method of increasing a time resolution according to an exemplary embodiment.

As illustrated in FIG. 7, the driving signal may be synchronized between first and second optical modulators 110 and 120, disposed with a distance d from one another. The driving signal of the first optical modulator 110 and the driving signal of the second optical modulator 120 may have the same period, but may have different phases. A phase difference between the driving signal of the first optical modulator 110 and the driving signal of the second optical modulator 120 may be "$\pi/(n*m)$" (where n is the number of optical modulators in a modulation device, and m is a natural number).

Since the driving signal of the first optical modulator 110 and the driving signal of the second optical modulator 120 have different phases, light incident onto the modulator array 100 may be shaped into a plurality of shape wavefronts according to the driving signal of the first optical modulator 110, and the plurality of shape wavefronts may be additionally shaped according to the driving signal of the second optical modulator 120. That is, light passing through the modulator array 100 may be controlled a plurality of times according to the driving signal of the first optical modulator 110 and the driving signal of the second optical modulator 120. When a detector having a time resolution earlier than the driving signal of the first optical modulator 110 is used, a modulation result of the second optical modulator 120 may be checked within a driving period time of the first optical modulator 110. As a result, in terms of the detector, an effect in which modulation shorter than a period of the first optical modulator 110 is performed is obtained in overall light modulation.

The above-described modulator array 100 may be applied to medical imaging apparatuses that acquire information about an object by using optical coherence. The space resolution of the modulator array 100 may be determined by a relative position relationship between the optical modulators with respect to the path of propagation of light or a cell arrangement of each modulator itself, and the time resolution of the modulator array 100 may be determined by a distance between the optical modulators or the driving signals of the optical modulators. Therefore, the medical imaging apparatuses may modulate light by adjusting a time, a space, a time resolution, or a space resolution depending on the case.

Figure 8:
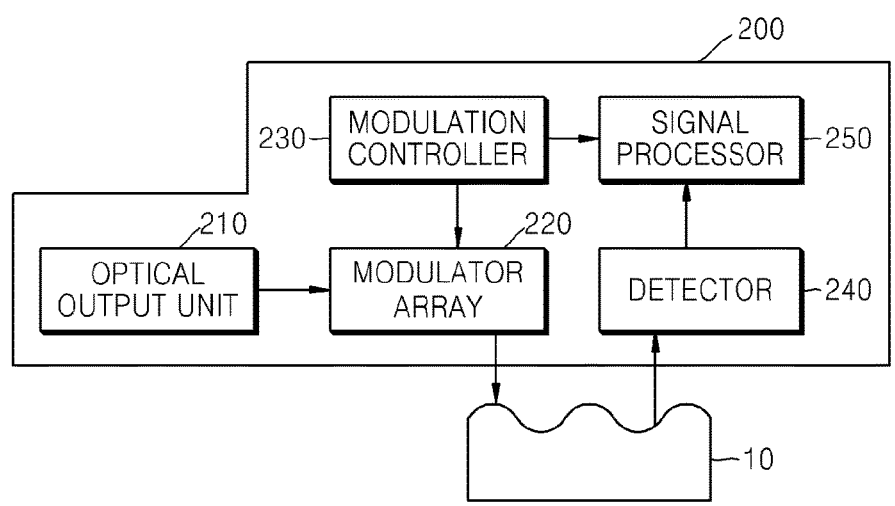
FIG. 8 is a block diagram illustrating a medical imaging apparatus according to an exemplary embodiment.

FIG. 8 is a block diagram illustrating a medical imaging apparatus according to an exemplary embodiment. Referring to FIG. 8, a medical imaging apparatus 200 includes an optical output unit 210, a modulator array 220, a modulation controller 230, a detector 240, and a signal processor 250. The medical imaging apparatus 200 of FIG. 10 is illustrated as including only elements relevant to the present exemplary embodiment. Therefore, it can be understood by one of ordinary skill in the art that the medical imaging apparatus 200 may further include general-use elements in addition to the elements of FIG. 8.

The medical imaging apparatus 200 according to the present exemplary embodiment is an apparatus that acquires a tomography image of an object by using light, and examples of the medical imaging apparatus 200 include all of the optical imaging apparatuses that may acquire a tomography image based on optical coherence, i.e., OCT apparatuses, OCM apparatuses, optical microscopes, etc.

The optical output unit 210 outputs light incident onto an object 10. In this case, the optical output unit 210 may output a wavelength-swept light, a laser, or the like, but is not limited to thereto. Light output from the optical output unit 210 passes through the modulator array 220, and is incident onto the object 10.

The modulator array 220 shapes light temporally or spatially. For example, the modulator array 220 may modulate a wavefront of light into a plurality of shape wavefronts, and may change the number of modulations. In this case, in the modulator array 220, an LCoS or a DM may be disposed on a path of propagation of light. The modulator array, which has been described above with reference to FIGS. 1-7 is applicable here, and, thus, its detailed description is not provided.

The modulation controller 230 may control modulation of light by adjusting at least one of a distance and a relative position between optical modulators of the modulator array 220 and driving signals of the optical modulators. For example, when intending to increase a space resolution, the relative position between the optical modulators may be adjusted. When intending to increase a time resolution, at least one of the distance between the optical modulators and the driving signals may be adjusted.

The detector 240 detects light acquired from light that passes through the modulator array 220 and is incident onto the object 10. The light acquired from the light incident onto the object 10 denotes light that is incident onto the object 10 and is acquired through transmission, reflection, and scattering. For example, the acquired light may be light that is acquired by coherence between reference light and response light acquired from the light incident onto the object 10. As another example, the acquired light may be light that is acquired by coherence between a secondary harmonic signal of the response light and a secondary harmonic signal of the reference light. However, the present exemplary embodiment is not limited thereto.

The signal processor 250 signal-processes a signal detected by the detector 240 to generate a tomography image. For example, the detector 240 may detect a spectrum signal corresponding to each shape wavefront, and the signal processor 250 may signal-process the detected spectrum signal to generate the tomography image.

The medical imaging apparatus 200 may further include an optical controller (not shown). The optical controller may determine a region of interest (ROI) corresponding to a transmission depth in which light is focused on the object 10, and control the light in order for the light to be focused on the determined ROI. The optical controller may determine a plurality of ROIs having different transmission depths in which the light is focused on the object 10. Therefore, the optical controller may control the light in order for the light to be sequentially focused on the plurality of ROIs.

Figure 9:
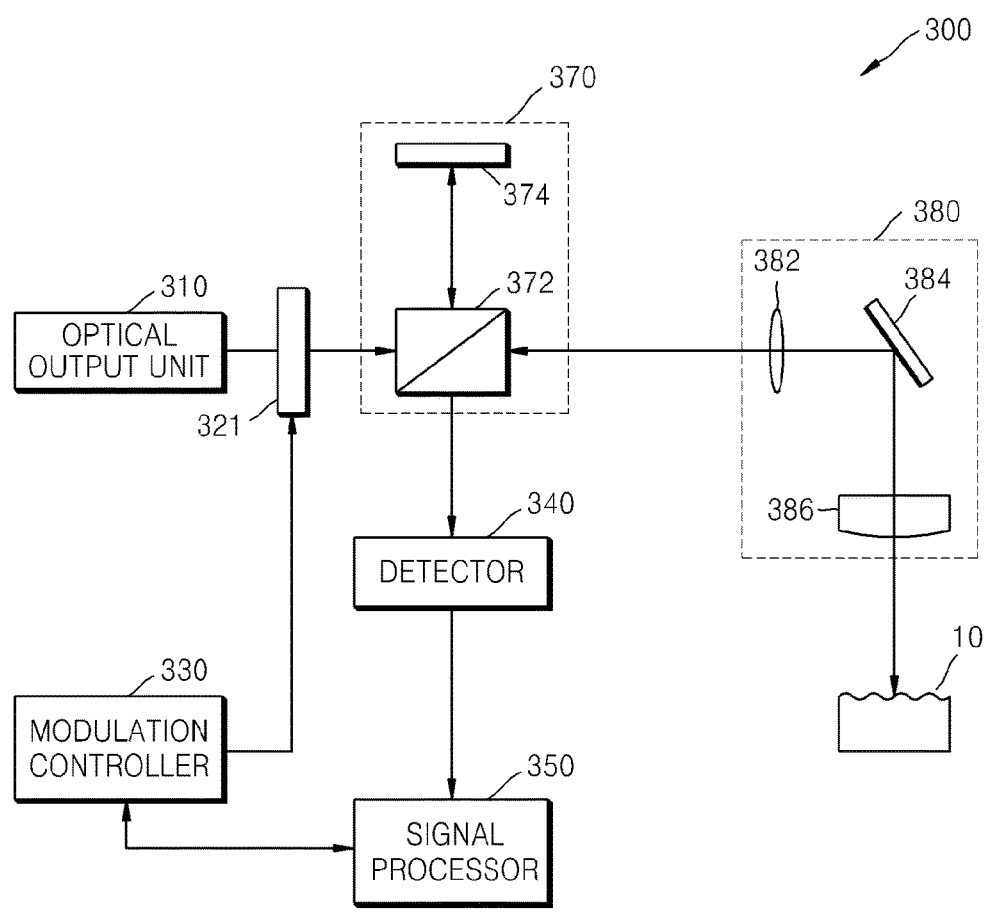
FIG. 9 is a diagram illustrating an optical coherence tomography (OCT) apparatus corresponding to an exemplary embodiment of the medical imaging apparatus.

FIG. 9 is a diagram illustrating an optical coherence tomography (OCT) apparatus 300 as an example of the medical imaging apparatus of FIG. 8. Referring to FIG. 9, the OCT apparatus 300 may include an optical output unit 310, a modulator array 321, a modulation controller 330, a detector 340, a signal processor 350, and may further include an interferometer 370 and an optical probe 380. The above-described details of the optical output unit 210, the modulator array 220, the modulation controller 230, the detector 240, and the signal processor 250 of FIG. 8 may be applied to the optical output unit 310, the modulator array 321, the modulation controller 330, the detector 340, and the signal processor 350 of FIG. 9, and thus, the same descriptions provided with regard to the elements are not repeated.

The optical output unit 310 transfers output light to the interferometer 370. According to an exemplary embodiment, the modulator array 321 may be disposed between the optical output unit 310 and the interferometer 370. Therefore, light having a phase obtained through modulation by the modulator array 321 may be transferred to the interferometer 370.

The modulator array 321 modulates a phase of light according to a relative position relationship and a distance between optical modulators of the modulator array 321 and driving signals of the optical modulators. The OCT apparatus 300 may modulate a phase of at least one of light emitted from the optical output unit 310, measurement light, and reference light. Referring to FIG. 9, the modulator array 321 of the OCT apparatus 300 may be disposed between optical output unit 310 and the interferometer 370, between a reference minor 374 and a beam splitter 372 of the interferometer 370, or at a position of the probe 380 on which the measurement light split by the beam splitter 372 is incident.

The modulator array 330 may adjust the relative position relationship and the distance between the optical modulators of the modulator array 321 and a delay of the driving signals according to a predetermined resolution. The predetermined resolution may be set by a user using the OCT apparatus 300, or may be automatically set according to a kind of an object.

The interferometer 370 splits light (which is output from the optical output unit 310) into the measurement light and the reference light, irradiates the measurement light onto the object 10, and receives response light generated from the measurement light reflected by the object 10.

The interferometer 370 may include the beam splitter 372 and the reference minor 374. Light transferred from the optical output unit 310 is split into the measurement light and the reference light by the beam splitter 372. Among the light obtained through split by the beam splitter 372, the measurement light is transferred to the optical probe 380, and the reference light is transferred to the reference mirror 384 and returns to the beam splitter 382. The measurement light transferred to the optical probe 380 is irradiated onto the object 10 of which an internal tomography image is to be captured by using the optical probe 380, and the response light generated from the measurement light reflected from the object 10 is transferred to the beam splitter 372 of the interferometer 370 through the optical probe 380. The transferred response light and the reference light reflected by the reference mirror 374 causes coherence in the beam splitter 372.

The optical probe 380 may include a collimator lens 382, a galvano scanner 384, and a lens 386. Here, the galvano scanner 384 is a mirror that rotates in a certain radius about a certain axis, and may be implemented with a micro electro mechanical system (MEMS) minor that obtains driving force necessary for rotation from an MEMS. The measurement light transferred from the interferometer 370 passes through the collimator lens 382 of the optical probe 380 to thereby be collimated. The collimated measurement light is reflected by the galvano scanner 384, and thus, a propagating direction of the measurement light is adjusted. The direction-adjusted measurement light passes through the lens 386, and is irradiated onto the object 10.

In the above descriptions of the medical imaging apparatus, an example using the OCT apparatus is provided, but the modulator array may be applied to various medical imaging apparatuses such as PAT apparatuses, OCM apparatuses, etc. In this case, a receiver may include a detection sensor suitable for a kind of a signal generated from an object, and an appropriate image signal processing method may be used.

According to the above-described exemplary embodiments, the modulator array shapes a wavefront of light by using a position relationship between a plurality of optical modulators and an arrangement relationship between cells included in each of the optical modulators, thereby increasing the space resolution of modulation. The modulator array controls a position or a driving signal of each of the optical modulators, thereby increasing the time resolution of modulation. The above-described optical probe may be applied to medical imaging apparatuses.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A modulator comprising:
a first optical modulator that includes first cells disposed adjacent one another in a plane across a path of propagation of light at a first position, each of the cells modulating a phase of light, into a first modulated light according to an applied voltage, wherein the light is incident on the first optical modulator and each of the first cells modulates the incident light by passing the incident light therethrough; and
a second optical modulator that includes second cells disposed adjacent one another in a plane across the path of propagation of light at a second position on the path of propagation of light, each of the second cells modulating a phase of the first modulated light into a second modulated light according to an applied voltage, wherein the first modulated light is incident on the second optical modulator from the first optical modulator and each of the second cells modulates the first modulated light by passing the first modulated light therethrough,
wherein a modulation resolution of the second modulated light output from the second optical modulator is greater than that of the first modulated light output from the first optical modulator, the second modulated light having been successively modulated by the first optical modulator and the second optical modulator.

2. A medical imaging apparatus comprising:
a light source;
the modulator of claim 1 that modulates light which is output from the light source; and
a probe configured to be inserted into a body cavity, and irradiate light, which is output from the modulator, onto an internal object of the body cavity.

3. The modulator of claim 1, wherein at least two first cells of the first optical modulator overlap one second cell of the second optical modulator with respect to the path of propagation of light.

4. The modulator of claim 3, wherein a partial portion of each of the at least two first cells respectively overlaps the one second cell.

5. The modulator of claim 1, wherein one first cell of the first optical modulator overlaps at least two second cells of the second optical modulator with respect to the path of propagation of light.

6. The modulator of claim 5, wherein the one first cell overlaps a partial portion of each of the at least two second cells.

7. The modulator of claim 1, wherein the first cells are arranged to be spatially shifted with respect to the second cells, in a direction across the path of propagation of light.

8. The modulator of claim 1, wherein at least one among the first cells and the second cells modulate light by varying a shape of at least one cell of the at least one among the first cells and the second cells or varying a position of a liquid crystal in at least one cell of the at least one among the first cells and the second cells.

9. The modulator of claim 1, wherein a first driving signal of the first optical modulator and a second driving signal of the second optical modulator are synchronized with each other in a temporally staggered manner.

10. The modulator of claim 9, wherein the first driving signal and the second driving signal are triggered at different times in a same period.

11. The modulator of claim 9, wherein a time difference between a triggered time of the first driving signal and a triggered time of the second driving signal is shorter than the same period.

12. An apparatus comprising:
a light modulator comprising:
a first optical modulator that includes first cells disposed adjacent one another in a plane across a path of propagation of light at a first position, each of the first cells modulating a phase of light into a first modulated light according to an applied voltage, wherein the light is incident on the first optical modulator and each of the first cells modulates the incident light by passing the incident light therethrough, and
a second optical modulator that includes second cells disposed adjacent one another in a plane across the path of propagation of light at a second position on the path of propagation of light, each of the second cells modulating a phase of the first modulated light into a second modulated light according to an applied voltage, wherein the first modulated light is incident on the second optical modulator from the first optical modulator and each of the second cells modulates the first modulated light by passing the first modulated light therethrough; and
a modulation controller coupled to the light modulator and configured to control a first driving signal of the first optical modulator and a second driving signal of the second optical modulator, to increase a modulation resolution of the light passing through the light modulator.

13. The apparatus of claim 12, wherein the modulation controller is further configured to control the first driving signal of the first optical modulator and the second driving signal of the second optical modulator, so that the modulation resolution of the second modulated light output from the second optical modulator is greater than that of the first modulated light output from the first optical modulator, the second modulated light having been successively modulated by the first optical modulator and the second optical modulator.

14. The apparatus of claim 12, wherein the modulation controller is further configured to control a time difference between the first driving signal of the first optical modulator and the second driving signal of the second optical modulator.

15. The apparatus of claim 14, wherein the time difference is shorter than a period of the first driving signal.

16. A panel comprising:
a first layer that includes first reflective cells disposed adjacent to one another and is configured to modulate light incident thereon into a first modulated light according to electrical signals respectively applied to each of the first reflective cells; and
a second layer that includes second reflective cells disposed adjacent to one another and is configured to modulate the first modulated light received from the first layer into a second modulated light according to electrical signals respectively applied to each of the second reflective cells,
wherein the first layer and the second layer are arranged so that a modulation resolution of the second modulated light is greater than that of the first modulated light due to at least two second reflective cells of the second layer that modulate light modulated by one first reflective cell of the first layer.

17. The panel of claim 16, wherein the first layer and the second layer are arranged so that one second reflective cell of the second layer modulates light modulated by at least two first reflective cells of the first layer.

18. The panel of claim 16, wherein at least one among the first layer and the second layer comprises at least one among a liquid crystal on silicon (LCoS) and a deformable mirror (DM).

19. The panel of claim 16, a first driving signal of the first layer and a second driving signal of the second layer are synchronized with each other in a temporally staggered manner.

20. The panel of claim 19, wherein a time difference between a triggered time of the first driving signal and a triggered time of the second driving signal is shorter than at least one of a period of the first driving signal and a period of the second driving signal.

\* \* \* \* \*